United States Patent [19]
Schindel et al.

[11] Patent Number: 5,824,908
[45] Date of Patent: Oct. 20, 1998

[54] NON-CONTACT CHARACTERIZATION AND INSPECTION OF MATERIALS USING WIDEBAND AIR COUPLED ULTRASOUND

[75] Inventors: David W. Schindel, Kingston, Canada; David A. Hutchins, Warwickshire, United Kingdom

[73] Assignee: Queen's University at Kingston, Kingston, Canada

[21] Appl. No.: 740,403

[22] Filed: Oct. 29, 1996

Related U.S. Application Data

[60] Continuation of Ser. No. 354,561, Dec. 12, 1994, abandoned, which is a division of Ser. No. 269,861, Jun. 30, 1994, Pat. No. 5,573,624.

[51] Int. Cl.[6] .................................................. G01N 29/00
[52] U.S. Cl. ............................ 73/632; 73/602; 73/644; 73/600; 73/598
[58] Field of Search ............................ 73/598, 600, 602, 73/606, 628, 629, 643, 644, 632

[56] References Cited

U.S. PATENT DOCUMENTS

| | | | |
|---|---|---|---|
| 3,662,589 | 5/1972 | Adler et al. | 73/602 |
| 4,265,122 | 5/1981 | Cook et al. | 73/627 |
| 4,307,611 | 12/1981 | Opara | 73/597 |
| 4,314,479 | 2/1982 | Spijkerman | 73/643 |
| 4,338,822 | 7/1982 | Yamaguchi et al. | 73/643 |
| 4,594,897 | 6/1986 | Bantz | 73/600 |
| 4,653,328 | 3/1987 | Herman | 73/602 |
| 4,674,332 | 6/1987 | Pace et al. | 73/597 |
| 4,702,112 | 10/1987 | Lawrie et al. | 73/629 |
| 4,901,577 | 2/1990 | Roberts | 73/600 |
| 5,218,869 | 6/1993 | Pummer | 73/629 |
| 5,309,765 | 5/1994 | Horigome et al. | 73/602 |
| 5,439,157 | 8/1995 | Geier et al. | 228/9 |

Primary Examiner—Hezron E. Williams
Assistant Examiner—Richard A. Moller
Attorney, Agent, or Firm—Richard J. Hicks

[57] ABSTRACT

A system for the non-contact inspection and characterization of an object in which wideband (40 kHz to approximately 2 MHz) air/gas coupled ultrasonic transducers are used. The system of the present invention enables a single set of transducers to be used in an inspection/defect detection arrangement to characterize materials having a wide range of through-thickness, and other resonances. For example, the through-thickness fundamental resonance of 11 mm thick plywood is 44 kHz, 723 kHz for 2 mm thick carbon fiber, and 1.47 kHz for 0.75 mm thick polystyrene, all of which are measurable in the same system. The system is used in a method to characterize a defect by being able to operate at or near the resonant frequency of the normal material and at or near the resonant frequency of the material in a defect region to improve the accuracy of detecting specific types of defects including inclusions, material thinning, delamination and pitting by monitoring changes of various attributes (e.g. amplitude, frequency) of the detected output signal. The system of the present invention can also be combined with laser or EMAT systems, where the means for generating ultrasonic vibrations in the object is a laser or EMAT and in pulse-echo arrangements in which a single wideband air-coupled transducer is used as the source and as the receiver/detector of ultrasound.

17 Claims, 9 Drawing Sheets

NON-CONTACT CHARACTERIZATION AND INSPECTION OF MATERIALS USING WIDEBAND AIR COUPLED ULTRASOUND

This application is a continuation of application Ser. No. 08/354,561, filed 12 Dec. 1994, now abandoned, which is a divisional of Ser. No. 08/269,861, filed 30 Jun. 1994 now U.S. Pat. No. 5,573,624.

FIELD OF THE INVENTION

This invention relates to the field of ultrasonic nondestructive testing of material. More particularly, this invention relates to non-contact inspection and characterization of materials using wideband ultrasonic air coupled capacitance transducers.

BACKGROUND OF THE INVENTION

Many types of basic building materials such as plastics, wood products and carbon-fibre reinforced polymers are manufactured as large sheets. During the manufacture of such material it is often required that the material be inspected to detect imperfections such as material thickness variation, delamination, pitting etc. In addition, it is also required that such material be inspected in use such as testing the composite integrity of the wing of an airplane.

Ultrasonic nondestructive testing (NDT) of material has been proposed in the prior art. Many conventional ultrasonic NDT techniques are performed by immersion of tested material in water to allow ultrasonic energy to be coupled from the transducers to the material. Alternatively, various liquid layers such as oil can be placed between the transducers and material surface to provide a type of contacting transducer. However, the use of liquid couplants is not permitted or desirable for some materials that can absorb or be contaminated by liquids. Moisture absorption may adversely affect the strength and the dimensional stability of critical components used in air and spacecraft for example.

As a result of the problems with conventional fluid immersion and contacting ultrasonic NDT techniques, non-contact systems have been proposed in the prior art. For example, electromagnetic acoustic transducers (EMAT), laser pulse generation techniques, and laser interferometric detection have been used in NDT environments. These methods involve non-contact generation and reception of ultrasound at the material surface.

However, the EMAT method requires proximity of the transducer to the material being tested, and the laser method has restrictions on the types of materials that can be studied. For example, in laser methods the material being tested must absorb the laser energy for generation of ultrasound but must reflect it for detection. Further, both of these methods have poor sensitivity as receivers of ultrasound.

One alternative method proposed in the prior art involves the generation and detection of narrow band ultrasonic waves in the material through an intermediary air/gas-gap, which has been termed the air-coupled method.

Specifically, an apparatus for NDT using narrow band air coupled ultrasound has been proposed in U.S. Pat. No. 4,594,897 issued to Bantz on Jun. 17, 1986 titled "Inspection of the Internal Portion of Objects Using Ultrasonics". Bantz describes a configuration that uses ultrasonic transducers having a piezoelectric layer that operates at other than half-wave resonance and a first matching layer of a coupling medium which operates at other than quarter-wave resonance. Only a second matching layer of the coupling medium operates in quarter-wave resonance at the operating frequency determined by the composite of the transducer-first layer thickness and acoustic impedance.

The system described by Bantz uses piezoelectric type air coupled transducers that have the following disadvantages:

(a) The piezoelectric air coupled transducer has an inherently narrow bandwidth (for example, a maximum of 200–500 kHz) and therefore operates only about the design centre frequency i.e. basically at a single frequency.

(b) This bandwidth limitation of the transducer means that a separate transducer would have to be used for different materials, and for thickness variations of the same material, in order to properly resonate the material being tested.

(c) If a defect has been detected, the Bantz system cannot be easily adapted to resonate the material at the defect resonant frequency, which can vary significantly (i.e. 200%), in order to rescan the material to obtain improved characterization of the defect.

In summary, prior art NDT air coupled systems using narrow bandwidth transducers generate useable data only in cases where the combination of thickness and sample velocity happen to yield a resonant vibration at or near the transducer's design centre frequency. Therefore, narrow band NDT air coupled techniques are greatly limited since they must be designed for a particular sample thickness and velocity i.e. with a particular application in mind.

Consequently, it would be desirable to provide an air/gas coupled system capable of operating over a wide frequency bandwidth to allow a wide range of materials to be inspected by the same system and without the need to change transducers. For example, since the resonant frequency of many building materials (wood, polystyrene etc.) will range from approximately 40 kHz to at least 2 MHz this would be a useful bandwidth. In addition, it would be desirable to provide an air coupled system which, by virtue of its wide bandwith is capable of improving the accuracy of detecting and characterizing specific types of defects including inclusions, material thinning, delamination, pitting etc.

OBJECT OF INVENTION

An object of the present invention is to provide a system for the inspection and characterization of imperfections or defects in a wide range of materials having resonant frequencies ranging from approximately 40 kHz to at least 2 MHz whereby the entire range of said frequencies can be achieved without changing transducers.

Another object of the present invention is to provide wide band air-gas coupled ultrasonic system for the inspection and characterization of a defect region in an object capable of improving the accuracy of detecting specific types of defects including inclusions, material thinning, delamination, and pitting.

BRIEF STATEMENT OF INVENTION

In accordance with one aspect of the present invention there is provided a system for the non-contact inspection and detection of a defect in an object comprising: generating means for stimulating ultrasonic vibrations in the object, said generating means being coupled to the object by a gaseous medium; receiving means for receiving ultrasonic energy emitted by the object, said receiving means being coupled to the object by a gaseous medium; means for converting the ultrasonic energy received by the receiving means into an electrical signal; processing means detecting any alteration in an attribute of the electrical signal which characterizes the presence of the defect; and wherein said receiving and generating means are operable over a wide range of frequencies from approximately 40 kHz to at least 2 MHz without the need to change transducer.

In accordance with another aspect of the present invention there is provided a system for the non-contact inspection and detection of a defect in an object comprising: a source of ultrasonic waves comprising a signal generator and a source transducer spaced from the object and coupled to the object by a gaseous layer, said source transducer having an aperture from which the ultrasonic waves propagate disposed at an angle relative to the object; a receiver transducer spaced from the object and coupled to the object by the gaseous layer to receive ultrasonic energy emitted by the object, said receiver transducer transducing the received ultrasonic energy into an electrical signal, whereby any alteration of an attribute of the electrical signal characterizes the presence of the defect; and wherein said source and receiver transducers are operable over a wide range of frequencies from approximately 40 kHz to at least 2 MHz without the need to change transducers.

In accordance with another aspect of the present invention there is provided a method for detecting and characterizing a defect region in an object comprising: (a) scanning the object using toneburst ultrasonic waves at approximately a first resonant frequency indicative of a selected characteristic frequency of the object to stimulate ultrasonic vibrations in the object; (b) detecting ultrasonic energy emitted by the object to generate a first signal; (c) monitoring an attribute of the first signal during said scanning for changes, wherein changes in the attribute of the first signal are representative of the existence of the defect region; (d) determining a second frequency based on the change in the attribute of the first signal, wherein said second frequency represents a selected other characteristic resonant frequency of the material in the defect region; (e) rescanning the object using toneburst ultrasonic waves at approximately the second frequency to stimulate ultrasonic vibrations in the object; (f) detecting ultrasonic energy emitted by the object to generate a second signal; (g) monitoring an attribute of the second signal for changes during said scanning, wherein changes in the attribute of the second signal are representative of transitions from the defect region to other regions of the object; wherein steps (a)–(c) are performed to determine if a defect region exists in the object, and steps (d)–(g) are performed to further characterize the defect region.

BRIEF DESCRIPTION OF THE DRAWINGS

Embodiments of the invention will be described by way of example in conjunction with the drawings in which.

DETAILED DESCRIPTION OF EMBODIMENTS OF THE INVENTION

The present invention is used for the non-contact characterization and inspection of materials that can include objects having solid plate or sheet type geometries, other regular or irregular geometries, and liquid media. In general the apparatus and method of the present invention can detect, image and characterize hidden flaws or other variations from a predetermined normal state termed the defect or defect region. The apparatus and method of the present invention can be used for on-line processing control of plastics, wood products, paper, carbon fibre reinforced composite materials, sheet metals and the like; and for non-destructive evaluations of materials employed in their respective application for example, aircraft wings, fuselages etc.

Figure 1:
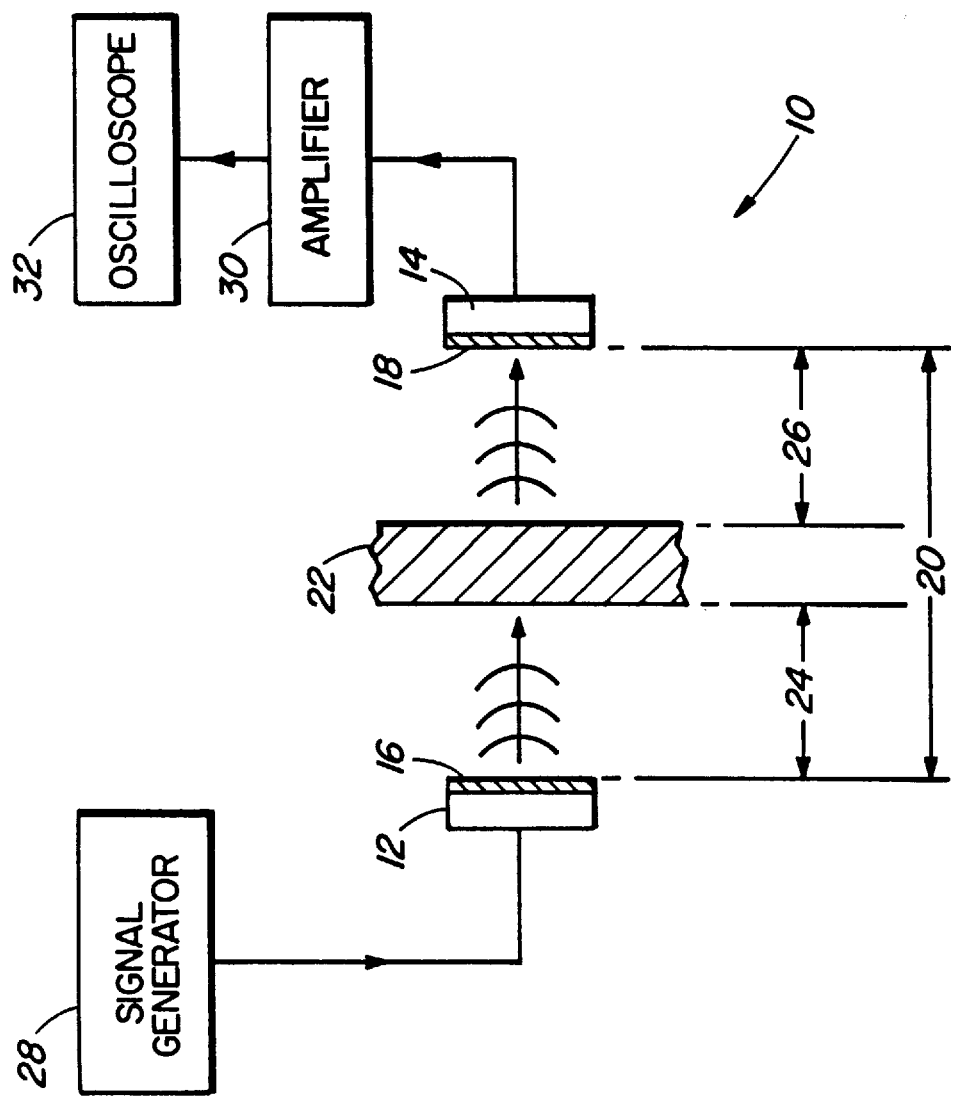
FIG. 1 is a schematic presentation of an inspection and characterization system according to one embodiment of the present invention.

FIG. 1 illustrates a normal incident non-contact testing system 10 according to one embodiment of the present invention.

Two wideband transducers, a source 12 and a receiver/detector 14, are aligned with their respective apertures 16 and 18 parallel, and separated by an air space 20. An object 22 is placed in the air space 20 to separate the air space 20 into two air gaps 24 and 26. A voltage is applied to the source transducer 12 by a signal generator 28 to excite the transducer 12 into generating ultrasonic waves.

The ultrasound emitted by the source transducer 12 propagates through the air gap 24 toward the object 22. Upon striking the boundary of the object 22, some of the ultrasound is transmitted into the object 22 where it travels with a higher velocity, termed the sample velocity. A fraction of the ultrasound in the object 22 will pass through the object 22 into the air gap 26 to arrive at the receiver/detector transducer 14.

In addition, a fraction of the ultrasound remains within the object 22 and undergoes multiple reflections and generates an air wave each time it strikes an air/sample boundary, which can also be detected by the receiver transducer 14. The measured first-arrival time and the frequency of air wave emission contain information (e.g. thickness, sample velocity) about the object 22 that can be used for material characterization. Specific examples relating to obtaining this information according to the present invention are detailed hereinbelow.

The receiver transducer 14 is located in a position such that the ultrasonic energy emitted from the object 22 is directed substantially normal to its aperture 18. The receiver transducer 14 transforms the airborne ultrasound into an electrical signal.

Depending on the object 22 being inspected and the desired wave propagation mode (e.g. Lamb, shear, longitudinal) the source 12 and receiver 14 transducers can be angled relative to a surface of the object 22.

The ultrasonic energy emitted by the object 22 is converted to an electrical signal by the receiver transducer 14 which is amplified and conditioned by an amplifier 30 and displayed on an oscilloscope 32. Should an imperfection be present in the object 22 between the point of entry of sound and the point at which the sound vibrations/energy are emitted, the receiver transducer 14 will respond with a change in its electrical output signal. This change in the output signal can be indicative of an imperfection or defect and is displayed by the oscilloscope 32. Changes in the output signal of the receiver 14 can be recorded as a function of the position of the object 22 to provide a representation of the defect.

The transducers 12 and 14 used in the present invention are disclosed in Applicant's U.S. Pat. No. 5,287,331 issued Feb. 15, 1994, titled "Air Coupled Ultrasonic Transducer", the disclosure of which is incorporated herein by reference. In general, the transducers consist of a thin metallized polymer membrane placed upon a micromachined silicon backplate. The backplate surface contains small etched pits that trap air and reduce the acoustic impedance of the backplate/membrane structure. The transducers can produce both focused and planar wavefields.

In the detection mode of transducer 14, movement of the membrane causes a change in induced charge on the backplate, to which a constant bias voltage is applied. In the generation of ultrasound by transducer 12, the applied voltage transient causes membrane motion. The response of both transducers 12 and 14 are well-damped with a bandwidth extending from approximately 40 kHz to at least 2 MHz, the upper limit depending on the thickness of the polymer film used in their construction, and the nature of the driving potentials applied during operation.

Based on the characteristics of the wideband transducers 12 and 14, the frequency (for example, from 40 kHz to at least 2 MHz) of the ultrasound generated from the source 12 can be chosen to excite the chosen resonance of the object 22 to increase transmission efficiency. In particular, the apparatus of the present invention can be used to inspect a wide range of materials having a wide range of resonance frequencies. For example, the system of FIG. 1 can inspect/characterize 11 mm thick plywood that resonates at 44 kHz, and without physically changing the transducers 12 and 14 can also inspect a polystyrene sheet of 0.75 thickness that resonates at 1.47 MHz. Further details of this wideband data range are discussed in Example 1 detailed hereinbelow.

Figure 2A:
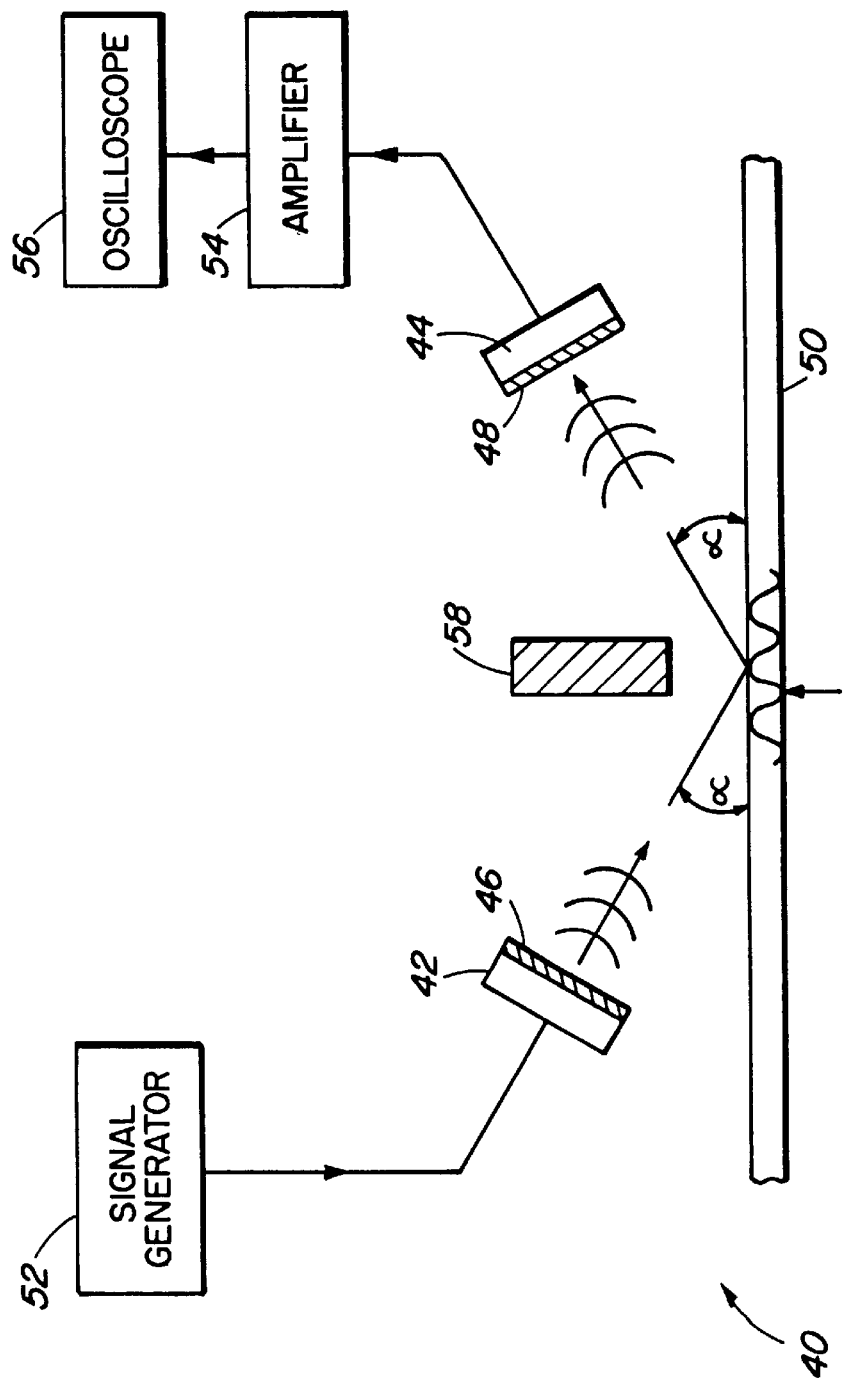
FIGS. 2A–2C are schematic presentations of inspection and characterization systems according to other embodiments of the present invention.

FIG. 2A illustrates a Lamb, Rayleigh or shear wave type inspection system 40 according to another embodiment of the present invention.

Two wideband transducers, a source 42 and a receiver 44, are aligned with their respective apertures 46 and 48 at an angle α to the object 50. A voltage is applied to the source transducer 42 by a signal generator 52 to excite the transducer 42 into generating ultrasonic waves.

The ultrasound generated by the source 42 directed towards the object 50 propagates in a direction to strike the object 50 at an incident angle α. It is well known in the art that at certain values of α, Lamb,Rayleigh or shear wave modes will be generated and propagated in the object 50. The preferred magnitude of the angle of incidence α is dependent upon several factors including thickness of material, frequency of operation and the desired wave mode generated in the object 50.

An absorbing material 58 can be placed in a region between the transducers 42 and 44 to effectively block the direct air-wave that propagates directly from the source transducer 42 to the receiver transducer 44.

The generated wave mode will propagate along the object 50 and radiate from the object 50 as an ultrasonic vibration at the same angle α toward the receiver transducer 44. Specifically, the wave propagates along the object 50, emitting an amount of ultrasonic energy into the adjacent air as it propagates.

The emitted ultrasonic energy received in the transducer 44 is converted into an electrical signal which is conditioned in a amplifier 54 and displayed in an oscilloscope 56. As discussed in conjunction with FIG. 1, aspects of the electrical signal can be recorded as a function of position of the object 50 as a means of representing any internal defects.

The system 40 of the present invention can not only vary the incident angle α, but more importantly can vary the source ultrasonic frequency at any angle α, as discussed in detail in conjunction with FIG. 1, to provide improved flexibility in the inspection process. In particular, the ability to vary the frequency at any angle α allows more wave modes to be investigated compared with narrow bandwidth piezoelectric air coupled transducer based systems.

Figure 2B:
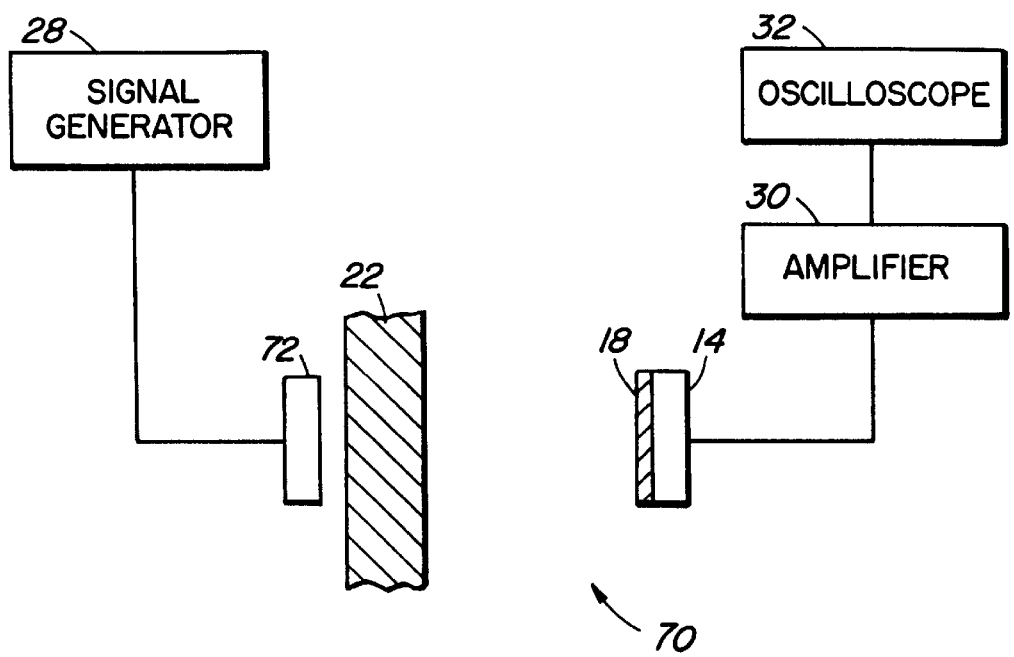
Figure 2C:
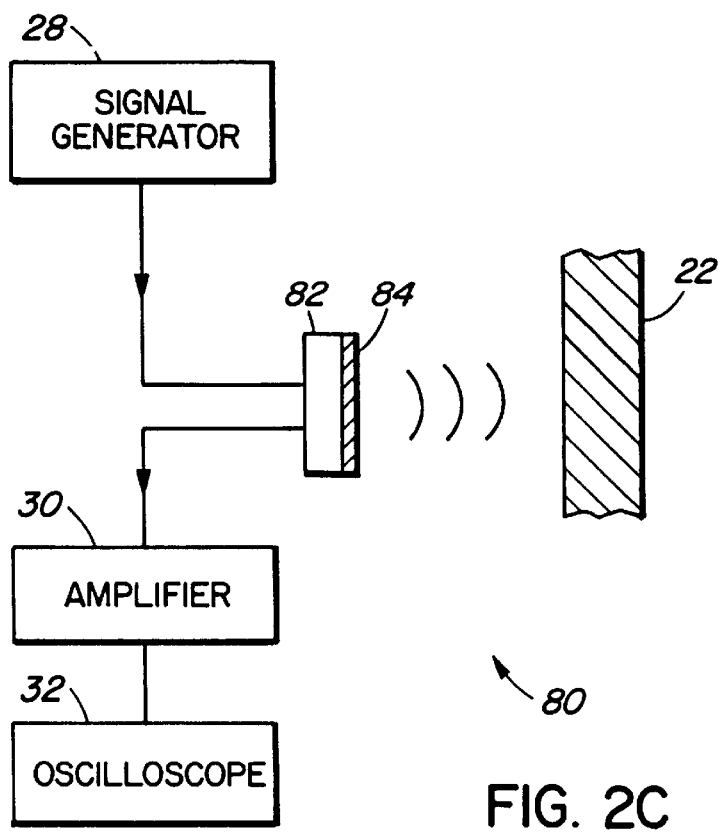

The systems 10 and 40 of FIGS. 1 and 2A uses two wideband transducers 12 and 14 to inspect the object 22 for defects; however, other configurations using only a single wideband transducer are illustrated in FIGS. 2B and 2C.

For example, FIG. 2B illustrates a hybrid system 70 in which the means for stimulating ultrasonic vibrations in the object 22 is accomplished by using a laser or EMAT 72. The EMAT 72 is connected to a signal generator 28 and is positioned adjacent a surface of the object 22 to generate ultrasonic vibrations in the object 22. This system can be applied to either systems 10 or 40. When a laser source is used for ultrasonic generation, two distinct modes are possible. The laser can provide a source through ablation or thermal expansion at the sample surface or by dielectric breakdown of the air adjacent to the surface. The ultrasonic vibrations/energy emitted by the object 22 are received by the transducer 14, conditioned by amplifier 30 and displayed by oscilloscope 32 in a manner similar to that described in conjunction with FIG. 1. It will be appreciated by those skilled in the art that the transmitted wave can alternatively be generated by an air coupled transducer and received by an EMAT or laser interferometer.

Another alternative system 80 is illustrated in FIG. 2C in which a single transducer 82 having an aperture 84 is used that operates as both a transmitter and as a receiver of ultrasound.

Using what is termed "pulse-echo" mode, the duration of the transmitted pulse from the transducer 82 must be timed to provide a quiescent period of transmission during which ultrasound reflected back to the transducer 82 may be received. The duration of the transmit pulse and quiescent period principally will be determined by the sound velocities in both air and the object 22 and the dual capability of the transducer 82. The signal generator 28, amplifier 30 and oscilloscope 32 provide the same functions as discussed in conjunction with the system 10 illustrated in FIG. 1.

The transducers 12, 14, 42, 44 and 82 are coupled to the object 22/50 by any gaseous medium at virtually any pressure. For example, ambient air is suitable for most applications; however, in certain circumstances other gases can be used at various pressures to improve coupling of the transducers to the object. For example, in some situations such as high frequency operation increasing the pressure of the coupling gas can result in improved ultrasonic coupling between the transducer(s) and the object being inspected.

The following examples illustrate a mode of operation in which the inspection system 10 of the present invention investigates the "through-thickness" resonance of the object 22, with the transducers 12, 14 at normal incidence with respect to the object 22. The examples will show that alterations of resonance amplitude will indicate flaws, and changes in frequency can be employed to characterize whether the flaws are inclusions, material thinning, backing members, delamination or the like.

EXAMPLE 1

Through-Thickness Measurements

Figure 3:
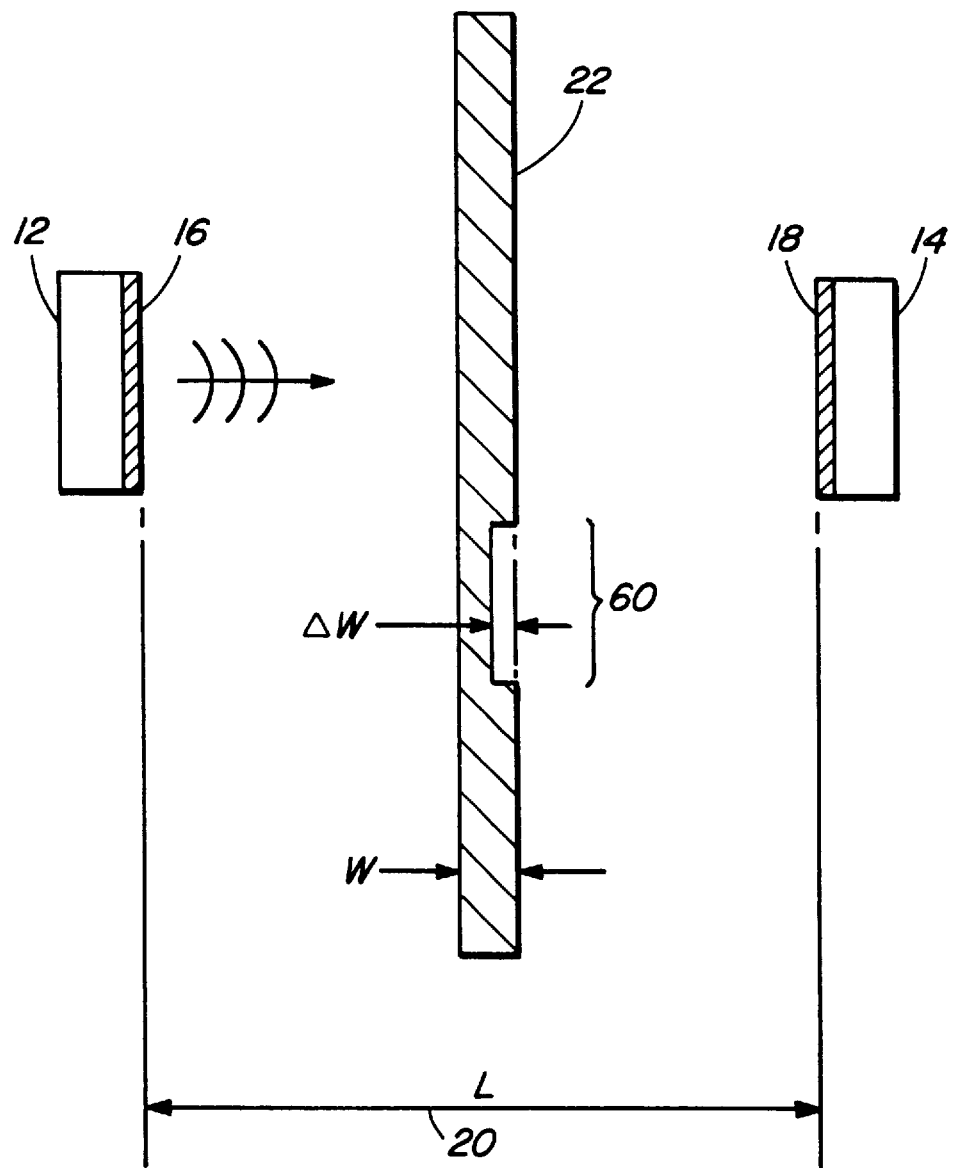
FIG. 3 is a specific schematic presentation of the system of FIG. 1 used in an experimental configuration.

The main components of an air coupled through-thickness system are shown schematically in FIG. 3. The signal generator, amplifier and oscilloscope are identical to that shown in FIG. 1 and are not represented for simplicity. The source transducer 12 and the receiver/detector transducer 14 are separated by air space 20 of length L. The object 22 having a thickness W is inserted in the air space 20. The object 22 has an ultrasonic longitudinal velocity $V_s$, which for most materials is much higher than the velocity of sound in air ($V_a \approx 345$ m/s). The object 22 may have a defect region 60 in which the object 22 thickness changes by $\Delta W$. The calculation of sample velocity and thickness changes will be discussed below for a wide range of materials.

Components and Configuration
  Source Transducer
  (a) Thickness of membrane: 6.3 $\mu$m
  (b) Aperture: 10 mm diameter
  (c) Insulator/Upper electrode: metallized Mylar
  (d) Lower electrode: silicon backplate with metallized gold film; backplate pits 40 $\mu$m in diameter and approximately 30 $\mu$m deep and placed on an 80 $\mu$m square grid
  Signal Generator
  Source Excitation
  Superposition of a 350 V DC bias voltage, and a –200 V wideband transient voltage from a standard Panametrics pulser-receiver. A capacitive decoupler was used to protect the pulser from the large DC bias applied to the source.
  Receiver/Detector Transducer
  (a) Thickness of membrane: 2.5 $\mu$m
  (b) Aperture: 10 mm diameter
  (c) Insulator/Upper electrode: metallized Mylar
  (d) Lower electrode: silicon backplate with metallized gold film; backplate pits 40 $\mu$m in diameter and approximately 30 $\mu$m deep and placed on an 80 $\mu$m square grid
  Amplifier
  (a) Output of detector transducer coupled to a Cooknell CA6/C charge sensitive amplifier with the bias voltage set at 100 V; output from the charge amplifier was fed to the receiving circuitry of the Panametrics pulser for additional 40 dB gain and elimination of low frequency noise by the 30 kHz high-pass filter to generate a conditioned signal.
  Oscilloscope
  (a) The conditioned signal is coupled to a Tektronix 2430A digital oscilloscope, which is triggered by the synchronization signal from the pulser.

No Sample
  The source and receiver apertures 16 and 18 of the transducers 12 and 14, respectively, were aligned parallel by maximizing the intensity and bandwidth of the multiple echoes in the air gap 20. This alignment step is performed to maximize the system's bandwidth.

Figure 4:
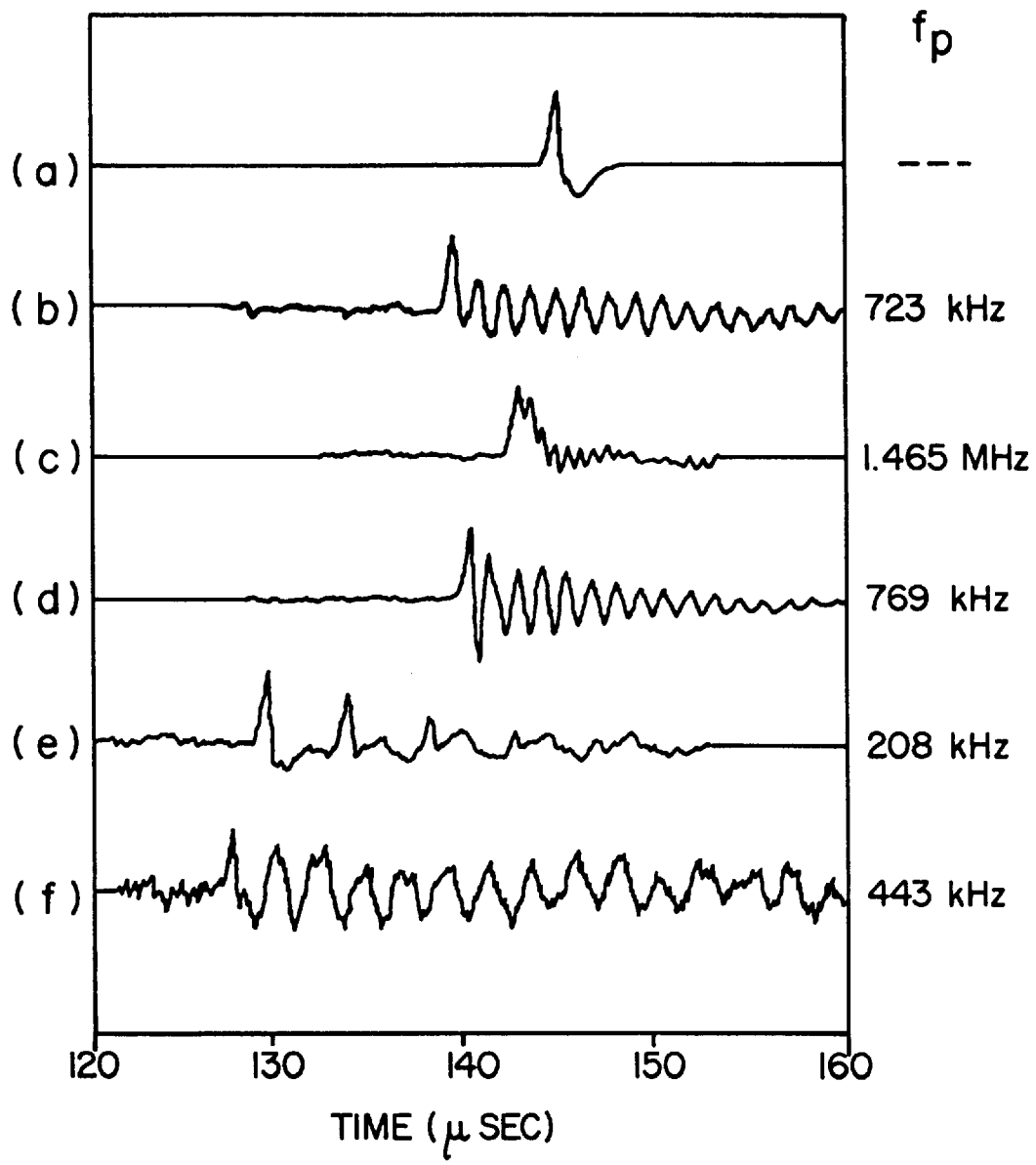
FIGS. 4 and 5 are graphical illustrations of response characteristics of various objects inspected in the system of FIG. 3 using pulsed excitation of the source transducer.

A typical signal resulting from this arrangement is shown in FIG. 4 signal line (a). The signal line (a) has an amplitude of approximately 2 V and is well-damped.

With Sample
  Table 1 summarizes the type of material and thickness used as test objects 22. An asterisk indicates that the sample includes a known thickness variation of $\Delta W$.

TABLE 1

Tested Materials

| SAMPLE Object 22 | THICKNESS (mm) |
|---|---|
| Carbon-fibre reinforced polymer (CFRP) Plate | 1.96 |
| Polystyrene | 0.75 |
| Plexiglass | 1.78 |
| Plexiglass | 5.88 |
| Glass | 5.96 |
| Masonite* | 2.78 |
| Solid Pine* | 13.22 |
| Particle Board* | 13.2 |
| Plywood | 11.13 |

A pulse of ultrasound is emitted by the source transducer 12 and propagates through the air toward the object 22. When the ultrasound strikes the object 22, some of the energy is transmitted into the object 22 where it travels with a higher velocity (i.e. the sample/object longitudinal velocity $V_s$). A fraction of the ultrasound will be transmitted through the object 22 into the air gap 20 to arrive at the receiver/detector transducer 14. However, a portion of the ultrasound wave will remain and be reflected within the object 22. Each wave reflection generates an air wave that can also be detected by the receiver/detector transducer 14.

The sample velocities and thickness changes of the objects listed in Table 1, were calculated using the time-of-flight method (i.e. first-arrival wave) and the frequency method (i.e. resonance of sample/object), discussed in detail below.

Quantitative Analysis of Sample Velocity and Thickness Change
  Sample Velocity: Time-of-flight Method
  The time of flight of the wave in the absence of the plate is defined as $t_a = L/V_a$ (Eq. 1). The first-arrival time with a sample inserted in the gap is defined as $t_w = (L-W)/V_a + W/V_s$ (Eq. 2). The time difference can then be defined as $t_a - t_w = W[(1-V_a/V_s)/V_a]$ (Eq. 3). From Eq. 3 the sample velocity can be determined as $V_s = V_a/[1 - V_a((t_a-t_w)/W)]$ (Eq. 4).
  Sample Velocity: Frequency Method
  The wave trapped within the object 22 leaks energy to the surrounding air each time it strikes an air/object boundary. This occurs on both sides of the object 22, although only the waves on the receiver 14 side will actually be observed.
  In the arrangement of FIG. 3 the frequency of the signal emitted by the object 22 is related to the through-thickness round trip transit time of the longitudinal wave by $f_p = V_s/2$ W (Eq. 5). The vibration $f_p$ is local to the region of incident ultrasound and corresponds to a free decay of the object's 22 through-thickness resonance.
  Thickness Change: Time-of-flight Method
  The time of arrival through the defect (thinned) region 60 of FIG. 3 is defined as $t_{w-\Delta w}$ (Eq. 6) with $t_{\Delta w} = t_{w-\Delta w} - t_w$ (Eq. 7). The thickness change can be determined through Eq. 7 and Eq. 3 as $\Delta W = t_{\Delta w} V_a/[1-(V_a/V_s)]$ (Eq. 8).

Thickness Change: Frequency Method

Estimation of the thickness changes is governed by the expression $\Delta W = V_s/2[(f_w - f_{w-\Delta w})/(f_w f_{w-\Delta w})]$ (Eq. 9), where $f_{w-\Delta w}$ and $f_w$ are the frequencies of the thinned region 60 and remaining regions of object 22 respectively.

Results

Figure 5:
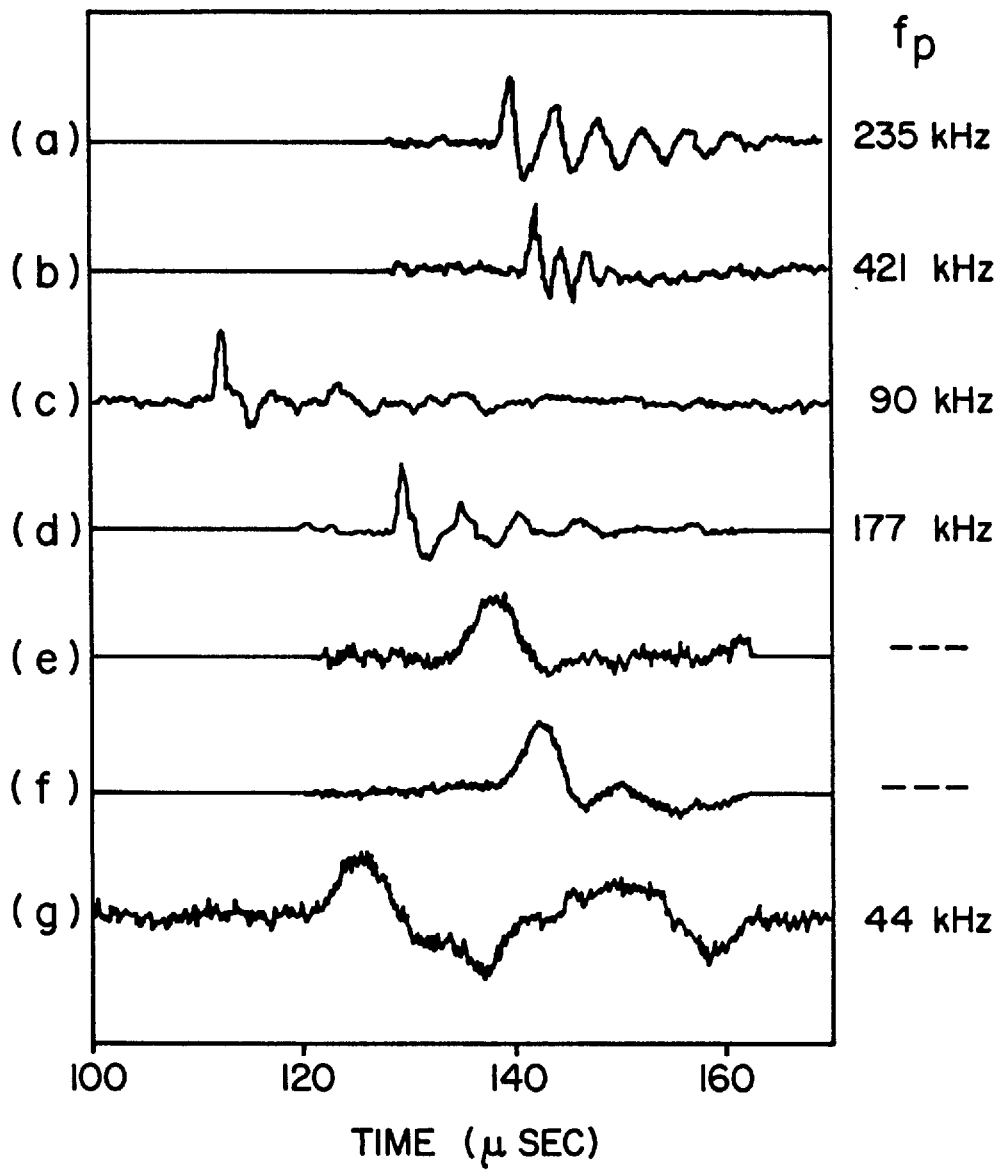

Signals arising from the insertion of the object/samples 22 of Table 1 within the gap 20 are shown in FIG. 4 waveforms (b)–(f), and in FIG. 5 waveforms (a)–(g). The sample velocity calculations for the samples of Table 1 using the two methods outlined above are summarized in Table 2.

In all of the tested samples, the time of first arrival occurred prior to the direct air wave indicated by the vertical dotted lines in FIGS. 4 and 5. The decaying oscillations after the first arrivals represent ultrasonic echoes within the object 22 samples themselves.

For example, FIG. 4 signal line (e) presents the results of the received signal in which the thickest plexiglass plate was placed in the gap 20 where the echoes within the sample are clearly separated. Where the resonance ($f_p$) is definable at some frequency this is stated in FIGS. 4 and 5 next to the signal line.

TABLE 2

Sample Velocity Comparison

| Sample Object 22 | Sample Velocity $V_s$ (m/s) | |
|---|---|---|
| | Time-of-Flight Method | Frequency Method |
| CFRP plate FIG. 4 signal (b) | 3928 ± 2424 | 2834 + 57 |
| Polystyrene FIG. 4 signal (c) | 2649 ± 2682 (−2649) | 2197 ± 105 |
| Plexiglass (1.78 mm) FIG. 4 signal (d) | 2232 ± 1044 | 2737 ± 103 |
| Plexiglass (5.88 mm) FIG. 4 signal (e) | 2858 ± 610 | 2670 ± 62 |
| Glass FIG. 4 signal (f) | 7191 ± 3208 | 5275 ± 62 |
| Masonite FIG. 5 signals (a) and (b) | 1161 ± 215 | 1307 ± 64 |
| Solid Pine FIG. 5 signals (c) and (d) | 2380 ± 381 | 2379 ± 89 |
| Particle Board FIG. 5 signals (e) and (f) | 466 ± 21 | ---------- |
| Plywood FIG. 5 signal (g) | 1113 ± 196 | 977 ± 71 |

FIG. 5 includes two signals for each of the masonite [(a)&(b)], pine [(c)&(d)], and particle board [(e)&(f)] object 22 samples. The pairing corresponds to the ultrasonic beam passing over the defect (thinned) region 60 of the object 22, and resulted in a shift of the waveforms toward the dotted line (direct air wave) and an increase in decay frequency. The thickness changes were estimated by the time-of-flight and frequency methods discussed above, and the results are summarized in Table 3. Independent measurements by vernier callipers are included for comparison.

TABLE 3

Thickness Change Comparison

| | Thickness Change $\Delta W$ (mm) | | |
|---|---|---|---|
| Sample | Vernier Calliper | Time-of-Flight Method | Frequency Method |
| Masonite | 1.1 ± 0.2 | 1.3 ± 0.3 | 1.2 ± 0.1 |
| Solid Pine | 6.6 ± 0.2 | 7.0 ± 0.4 | 6.5 ± 0.9 |
| Particle Board | 5.9 ± 0.3 | 6.3 ± 3.6 | --------- |

Summary

The advantages of the present invention can be seen from the wide range of information provided in the waveforms of FIGS. 4 and 5. Specifically, the resonant frequencies in the data range from 44 kHz in the FIG. 5 waveform (g) up to 1.465 MHz in the FIG. 4 waveform (c).

EXAMPLE 2

Toneburst Excitation at the Resonant Frequency

Components and Configuration

Same components and configuration as detailed in Example 1. However, a 30 V toneburst excitation voltage whose carrier frequency could be varied, was applied to the source transducer 12 via a Wavetek function generator. This voltage was superimposed upon a 350 V bias for linerization of the source transducer 12. The tested object 22 was a sheet of plexiglass of 1.78 mm thickness.

Determining Through-thickness Resonance

Figure 6A:
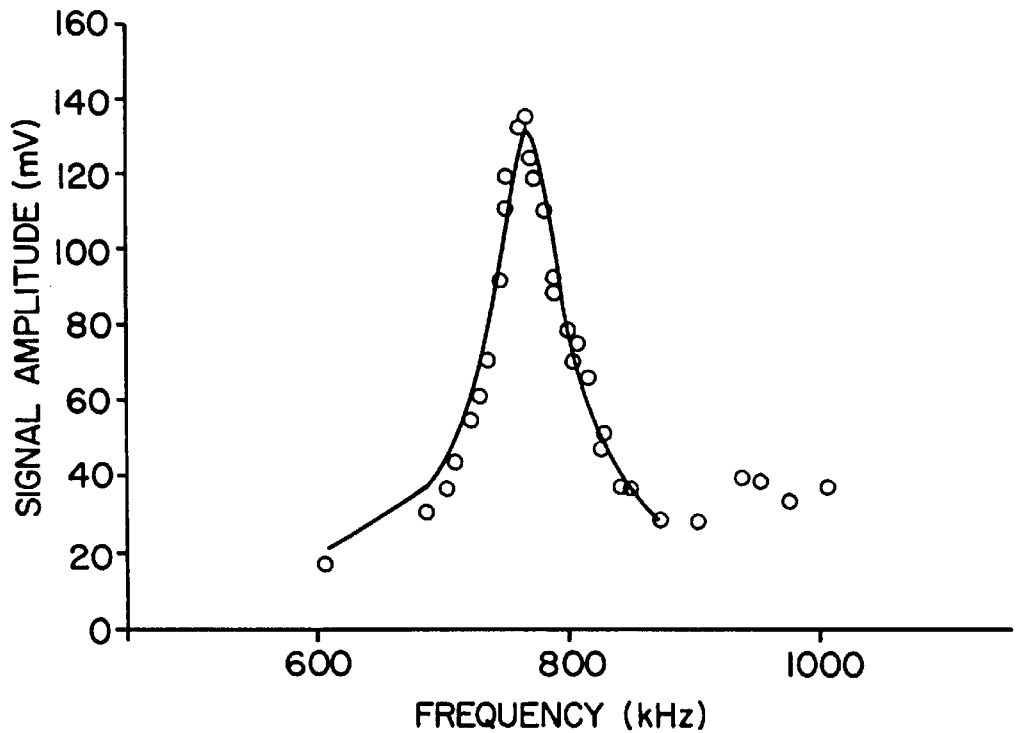
FIG. 6A is a graph of a frequency response characteristic curve near the fundamental through-thickness resonance for a specific sample inspected in the system of FIG. 3 using toneburst excitation of the source transducer.

When the toneburst frequency matched the through-thickness fundamental resonance of the object 22, the signal amplitude received at the receiver/detector transducer 14 increased to approximately 140 mV, as shown in FIG. 6A.

Similar increases in amplitude can also be observed at frequencies associated with harmonics of the fundamental through-thickness resonance (i.e. often at integral multiples of the fundamental frequency), although the present example examines the variations of the output signal at the fundamental frequency.

Discussion

Figure 6B:
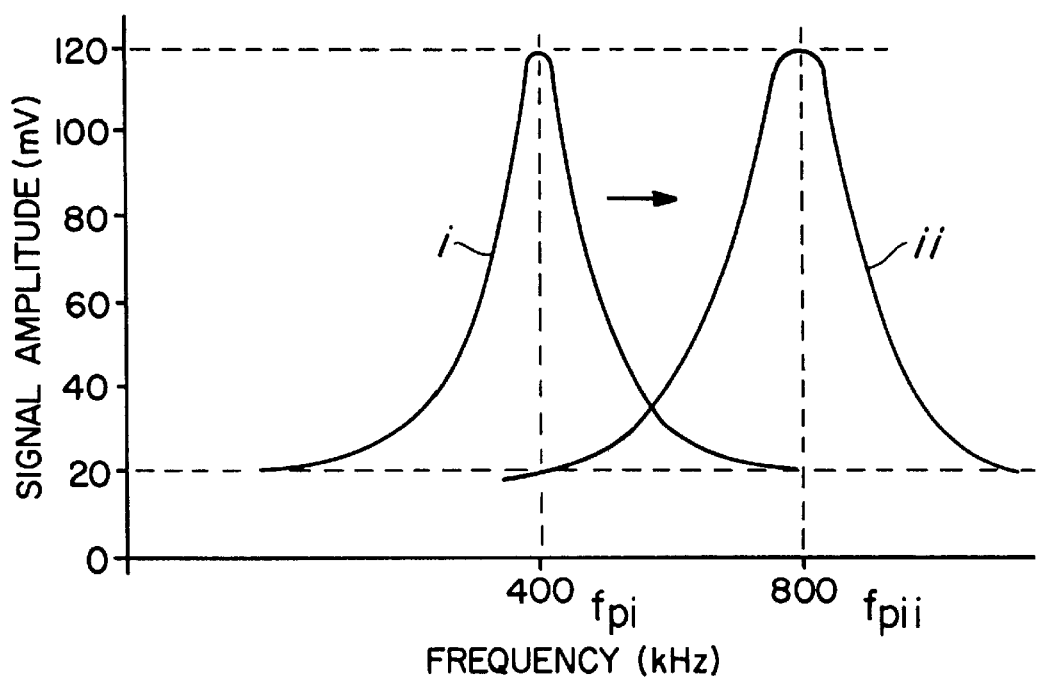
FIG. 6B is a graph of two frequency response characteristic curves of the same material representing the shift into a defect region.

As used herein, the term "toneburst excitation" means a finite length time window containing a single frequency sinusoid. In other applications a "chirp" may be substituted for a tone burst, in which case the frequency varies throughout the time window. To illustrate the flexibility of the inspection system of the present invention using toneburst excitation, FIG. 6B illustrates a frequency response characteristic curve i for a material having a fundamental resonance frequency ($f_{pi}$) of approximately 400 kHz and a peak signal amplitude of 120 mV.

As the object 22 is scanned relative to the source 12 (by moving the transducers 12, 14 relative to the object 22 or by moving the object 22 relative to the transducers 12, 14) the source transducer 12 is excited to generate a toneburst frequency of 400 kHz. During the scan variations of signal amplitude (i.e. a deviation from the peak of 120 mV) are monitored. If there is a drop in the signal amplitude (for example to 20 mV), then it could be an indication that some type of defect has been encountered in the object 22.

In the simplest case, where the defect region 60 is a thinned region, the drop in signal amplitude at the receiver 14 is due to a shift in the curve i represented by another frequency response characteristic curve ii of the defect region 60. This occurs because the object 22 has a different through-thickness resonance in the defect region 60. Since the inspection is being conducted at 400 kHz, the ultrasound passing through the defect region 60 results in a signal amplitude of the receiver 14 of only 20 mV.

In order to better characterize the type of defect encountered in the object 22 the object 22 can be inspected again at the resonant frequency of the defect region 60 (i.e. $f_{pii}$=800 kHz). This can be accomplished merely by changing the signal generator excitation of the wideband source transducer 12.

During the rescan the defect region 60 will return a high signal amplitude (120 mV) and the non-defect region of the object 22 will return a lower signal amplitude (20 mV). By monitoring and/or imaging the output signals it is possible to better characterize the defect region 60. (refer to Example 3)

Example 2 relates specifically to operating at the fundamental through-thickness resonance of the sample being inspected. However, as noted hereinabove higher harmonics of the fundamental through-thickness resonance can also be used for determining specific details relating to the defect region 60 such as depth of thinning, pitting etc. Further, using the systems 10 and 40 of the present invention other output signal characteristics, apart from signal amplitude, can be studied such as the change in shape of the characteristic curves, velocity dispersion, frequency variations and the like.

As a result, by using such methods it is possible to improve the accuracy of detecting specific types of defects including inclusions, material thinning, delamination, pitting etc.

EXAMPLE 3

Imaging Defects

Components and configuration similar to Example 2 with the following exceptions:

(a) Replace the low voltage function generator by a Matec gated amplifier to provide a dramatic increase in signal level.

Figure 7A:
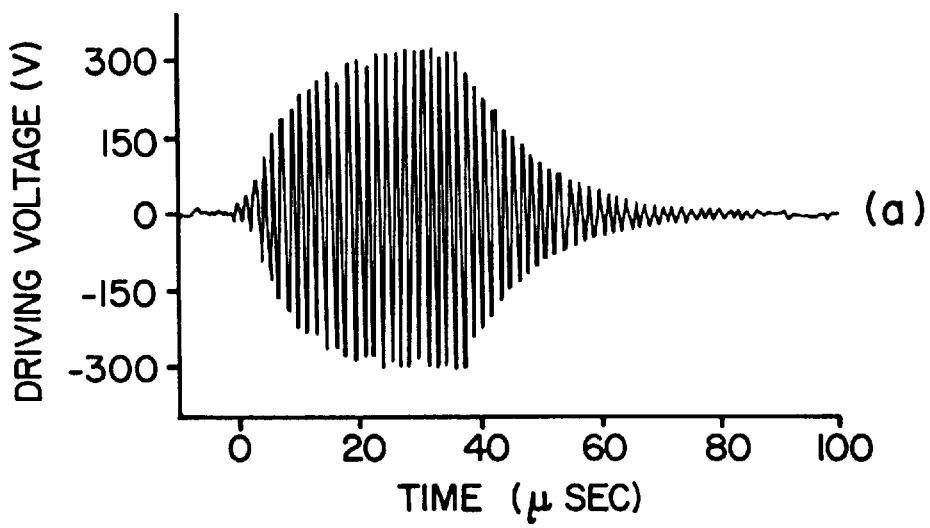
FIG. 7A is a graphical representation of a toneburst excitation signal applied to the source transducer.

(b) The excitation voltage applied to the source transducer 12 consists of a 600 V (p-p) toneburst as shown in FIG. 7A.

Sample
(a) 1.96 mm thick CFRP plate
(b) 16-ply quasi-isotropic plate
(c) two defects were present in the plate:
  DEFECT 1: a square piece of thin Teflon tape (2.54 cm square by 125 $\mu$m thick) which had been integrated into the mid-plane of the laminate during lay up. The location of the tape was not evident by visual inspection of the plate as the tape was carefully made to replace the central fibers.
  DEFECT 2: an impact damage on the external surface of the plate which produced an approximately 200 $\mu$m deep, spherical indent of approximately 5 mm in diameter.

(c) The toneburst frequency was matched to the sample's through-thickness resonance in a region where no defects were present, namely 723 kHz (see FIG. 4 waveform (b)). The sample plate could then be raster scanned between the transducers by a scanning system under computer control (not shown), with the amplitude of the received signal being recorded as a function of position.

Results

Figure 7B:
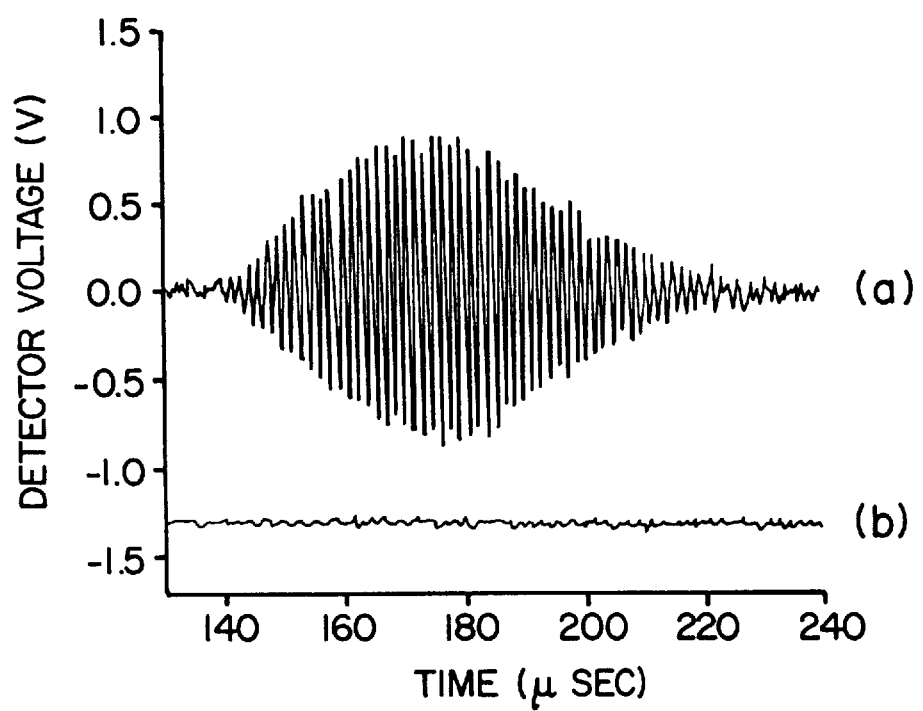
FIG. 7B is a graphical representation of (a) receiver/detector transducer response over a non-defect region; and (b) receiver/detector transducer response over a defect region for the system of FIG. 3 with the source excitation by the toneburst of FIG. 7A.

In the region surrounding the defect 60, the signal amplitude was 1.8 V (p-p) (FIG. 7B waveform (a)) but dropped to the background noise level of approximately 80 mV (p-p) (FIG. 7B waveform (b)) at defects 1 and 2.

Figure 8A:
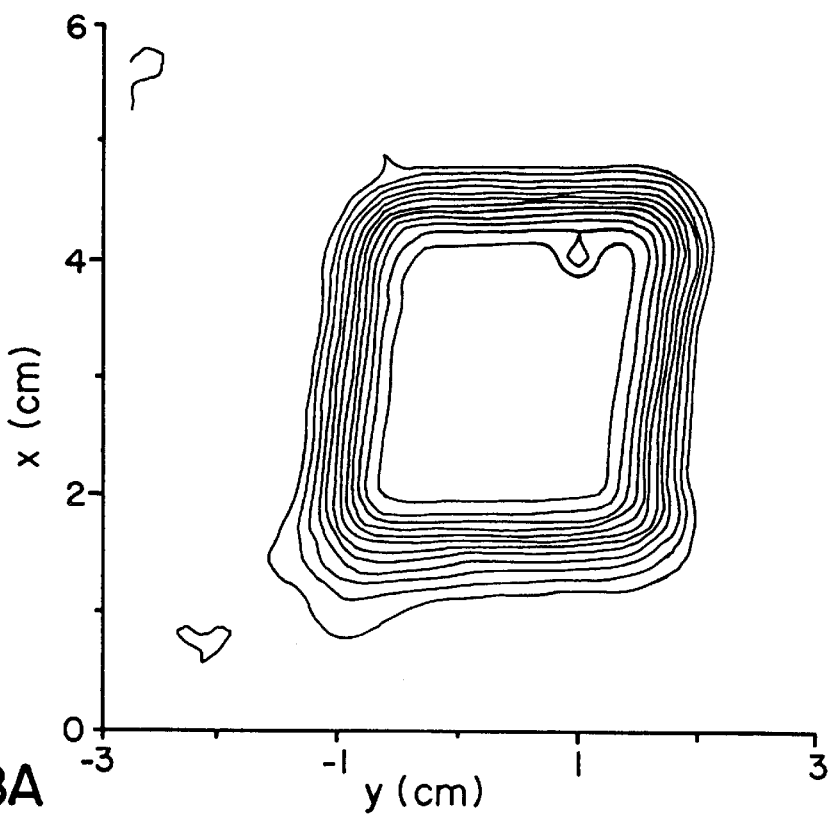
FIGS. 8A and 8B are graphical representations of defects in an object inspected according to system of FIG. 1.
Figure 8B:
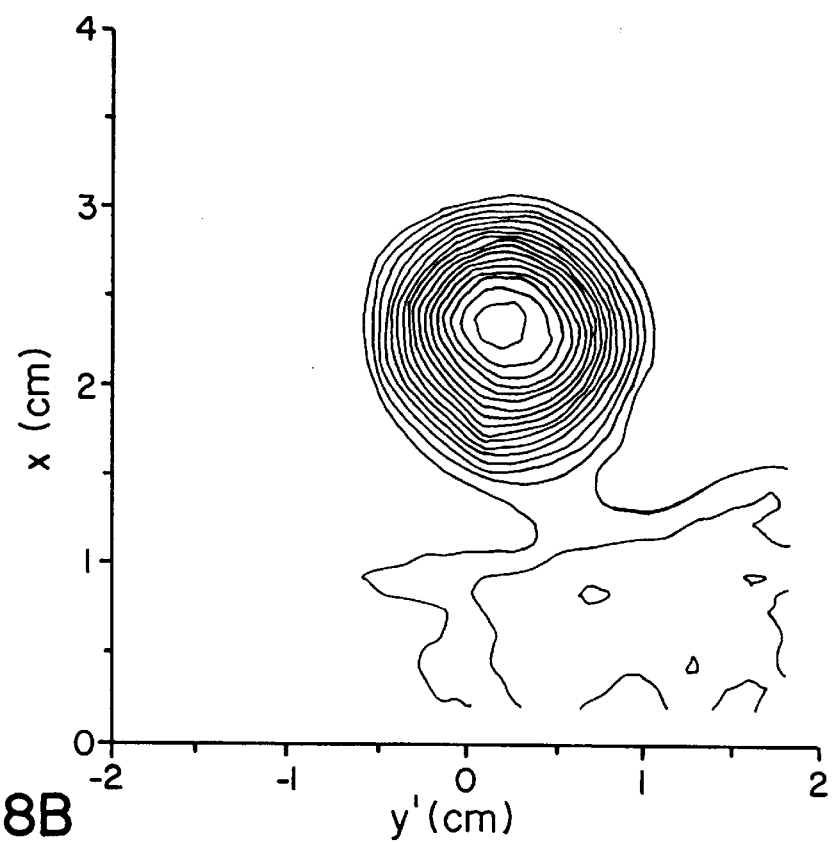

Scans of the two defects are shown in terms of received amplitude in the contour maps of FIG. 8A (Defect 1) and FIG. 8B (Defect 2), where their positions, shapes, and orientations are clearly visible.

Discussion

Imaging example 3 illustrates the functionality of the system and method of the present invention when operating at the through-thickness resonance, but the same system can be used for samples of different material having thicknesses ranging from fractions of a millimetre and up without the need to custom design and refit the transducer arrangement. In addition, the toneburst frequency can be set at any frequency within the wideband operating range of the transducers (for example, from approximately 40 kHz to at least 2 MHz).

The contour graphs for FIGS. 8A and 8B illustrate the relationship between detector signal amplitude variations as a function of object position; however, other output signal attributes or parameters can be used for imaging various aspects of the defect region 60 in the object 22. For example, feedback electrical connections can be included in systems 10 and 40 (between the amplifier output and the signal generator) to allow a feeding back of various aspects of the detected signal for control of the source transducer and its generating characteristics. Specifically, to monitor frequency variations in the output signal, as opposed to amplitude variations, the use of lock-in or phase-sensitive techniques can be used to track the resonant frequency of the sample as a function of position.

As illustrated by Examples 1–3, the system of the present invention enables improved flexibility in the inspection and characterization of materials in non-contact air coupled ultrasonic techniques.

We claim:

1. A system for the non-contact inspection and detection of a defect in an object comprising:
  generating means for stimulating ultrasonic vibrations in the object, said generating means being coupled to the object by a gaseous medium;
  receiving means for receiving ultrasonic energy emitted by the object, said receiving means being coupled to the object by a gaseous medium;
  means for converting the ultrasonic energy received by the receiving means into an electrical signal;
  processing means detecting any alteration in at least a selected portion of the electrical signal which characterizes the presence of the defect; and
  wherein said receiving and generating means have wideband frequency responses and are operable at all frequencies between approximately 40 kHz and at least 1.465 MHz.

2. The system of claim 1, wherein said generating means and said receiving means comprise a single transducer, said transducer having an aperture from which ultrasonic waves propagate and to which the ultrasonic energy is received.

3. The system of claim 1, wherein the generating means includes a signal generator and a source transducer, said source transducer having an aperture from which ultrasonic waves propagate, and said source transducer being operable over a range of frequencies from approximately 40 kHz to approximately 2 MHz.

4. The system of claim 1, wherein the gaseous medium is ambient air.

5. The system of claim 1, wherein the object is in the form of a continuous body of material, and further including means for moving the object relative to the generating means and receiving means to provide for continuous inspection of the object.

6. The system of claim 1, further including signal processing means for amplifying the electrical signal generated by the receiving means to produce a conditioned output signal.

7. The system of claim 6, further including display means for displaying the conditioned output signal from the signal processing means.

8. The system of claim 1, wherein the generating means and the receiving means are positioned on opposite sides of the object.

9. The system of claim 8, wherein the source transducer and the receiver transducer are located at an angle of 90° relative to a surface of the object.

10. The system of claim 8, wherein the generating means and the receiving means are located at an acute angle relative to a surface of the object.

11. The system of claim 1 wherein both the generating means and the receiving means are located on the same side of the object.

12. The system of claim 11, wherein the apertures of the source transducer and the receiver transducer are located at an acute angle relative to a surface of the object.

13. The system of claim 1, wherein the gaseous medium is ambient air.

14. The system of claim 1, including means for imaging a first electrical signal as a function of the position of the object so as to provide a visual representation of the defect region.

15. The system of claim 1 including means for imaging a second electrical signal as a function of the position of the object so as to provide a visual representation of the defect region.

16. The system of claim 1 wherein the electrical signal includes amplitude and attenuation characteristics.

17. The system of claim 1 wherein the electrical signal includes frequency characteristics.

* * * * *